United States Patent
Cetinkaya

(10) Patent No.: US 11,147,941 B2
(45) Date of Patent: Oct. 19, 2021

(54) SYSTEM AND METHOD USING WHITE NOISE FOR CALMING CRYING INFANT

(71) Applicant: Senay Cetinkaya, Adana (TR)

(72) Inventor: Senay Cetinkaya, Adana (TR)

( * ) Notice: Subject to any disclaimer, the term of this patent is extended or adjusted under 35 U.S.C. 154(b) by 0 days.

(21) Appl. No.: 15/758,018

(22) PCT Filed: Jun. 15, 2017

(86) PCT No.: PCT/TR2017/050265
§ 371 (c)(1),
(2) Date: Mar. 7, 2018

(87) PCT Pub. No.: WO2018/226174
PCT Pub. Date: Dec. 13, 2018

(65) Prior Publication Data
US 2020/0222657 A1    Jul. 16, 2020

(30) Foreign Application Priority Data

Jun. 6, 2017  (TR) ................................ 2017/08323

(51) Int. Cl.
*A61M 21/02* (2006.01)
*A61B 5/0533* (2021.01)
*A61B 5/00* (2006.01)
*A61M 21/00* (2006.01)

(52) U.S. Cl.
CPC ........... *A61M 21/02* (2013.01); *A61B 5/0533* (2013.01); *A61B 5/7282* (2013.01); *A61B 2503/04* (2013.01); *A61M 2021/0027* (2013.01)

(58) Field of Classification Search
CPC .......... A61M 21/00; A61M 2205/3375; A61M 2230/06
See application file for complete search history.

(56) References Cited

U.S. PATENT DOCUMENTS

| | | | |
|---|---|---|---|
| 2013/0123572 A1 | 5/2013 | Eliasi | |
| 2015/0045608 A1* | 2/2015 | Karp | A61M 21/02 600/28 |
| 2015/0083141 A1* | 3/2015 | Hertle | A61F 11/14 128/866 |

(Continued)

FOREIGN PATENT DOCUMENTS

WO    WO-2016/164373 A1    10/2016

OTHER PUBLICATIONS

International Search Report for Application No. PCT/TR2017/050265, dated Feb. 19, 2018.

(Continued)

*Primary Examiner* — Christine H Matthews
(74) *Attorney, Agent, or Firm* — Bayramoglu Law Offices LLC

(57) ABSTRACT

A method for calming a crying of a baby using a computer system having a memory, a microprocessor, a voice and digital visual display, and a user interface, the method comprising: providing a recording of white noise to a media player or to the computer system, providing a sensor in communication with the microprocessor, wherein the sensor is configured for measuring muscle contractions of a baby, and instructing, in response to a predetermined number of muscle contractions of the baby, the recording of the white noise to be played into headphones on ears of the baby.

6 Claims, 1 Drawing Sheet

(56) References Cited

U.S. PATENT DOCUMENTS

2015/0092972 A1* 4/2015 Lai .................. H04R 1/1008
                                                    381/333
2016/0270718 A1   9/2016 Heneghan et al.
2017/0182284 A1*  6/2017 Ueya .................. G06F 3/165

OTHER PUBLICATIONS

John E. Hall, Guyton and Hall Textbook of Medical Physiology, 2010, Twelfth Edition, Saunders Elsevier.

* cited by examiner

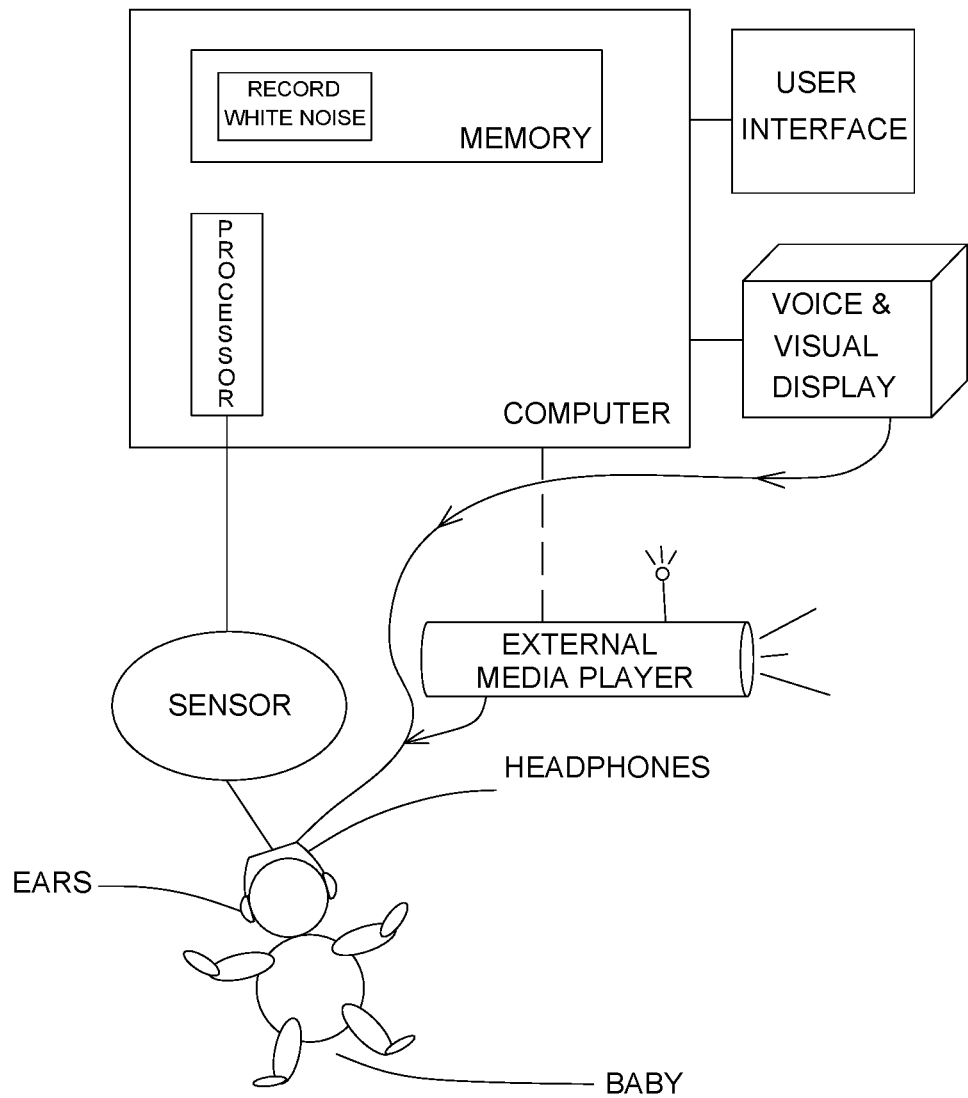

SYSTEM AND METHOD USING WHITE NOISE FOR CALMING CRYING INFANT

TECHNICAL FIELD

Invention is about a device which provides babies to calm down without any parent intervention by making them listen to the white noise installed to its memory by pre-determining of their cry with the change in their breathing and the vibration occurs during crying.

BACKGROUND

Colic is a very common complaint in the first three months after birth that is defined as uneasiness and never ending crying seizures that last for more than three weeks, at least three days a week, and three hours a day. This situation is seen in 5-25% of infants. It usually starts in the second to third weeks after birth, increases in the sixth to eighth weeks, and resolves by itself in the third to fourth months. Colic crying is different from normal crying; the baby can weep for hours without calming down. In very few children, crying lasts for 24 hours. Crying seizures are usually observed after lunch or in the evening. Usually, colic crying is repeated every day, sometimes it pauses overnight. During the seizures, a painful expression occurs on the face of the baby, the fists are tightened and the legs are pulled to the stomach. The characteristic seizure starts suddenly and loud and constant crying is observed. Babies with colic pain create a crisis situation in the family. It causes stress in the family, it can even distort the family balance. Because the baby is crying, the parents are restless and unhappy. Babies and family cannot sleep either. It may negatively affect the working efficiency of the working parent and the growth and development of the baby. In a study of babies with colic, it has been found that white noise reduces babies' cry out, cry and the time they stay awake, while improving their nutrition and sleeping times (1). In other studies, it is also shown that white noise is effective on pain (2, 3). It is also noted in the literature that it is the relaxing effect of white noise (4).

Spencer et al. (1990) found that in their study with 20 babies, white-noise increases the sleep durations (5). Muenssinger et al. (2013) found that babies in the mother's womb reacted most to the white noise stimulus in their work with the fetuses (6).

White noise is also called white sound. White noise consists of a combination of sounds at all different frequencies. It can be described as a buzz of 20,000 different tones at once. White noise sounds like the frequency and signal of the wind coming through the trees, waterfall, radio waves or signals and frequencies that resemble ocean waves. Besides, it is found similar to the sounds in the mother's womb by the baby because of the white noise's buzzing and continuous monotone sound. These sounds are similar to the sounds in the baby's mother's womb and comforts the babies. There is also a white noise CD prepared by musician Orhan Osman. This CD contains sounds such as heart beats, musical instruments and water sounds.

It has been observed that infants with colic calm down by listening to different frequency sounds such as from a hair dryer and an electric vacuum cleaner. In addition, various studies such as calming babies with colic, reducing sedation and anxiety during surgical operation, calming the baby during painful procedures and examining the effect on baby's movements in mother's womb via white noise have been done.

SUMMARY

Invention is about applying electrodes, which comprise Galvanic Skin Response (GSR) sensors, to the abdominal region of a baby, thereby detecting cramp-like pains and sending a signal to the microprocessor to start playing white noise. Thus, the object of the patent application is to provide the process of calming babies with colic to be completed without parental intervention.

BRIEF DESCRIPTION OF THE DRAWINGS

FIG. 1 is a schematic diagram showing an embodiment of the system of the invention.

DETAILED DESCRIPTION

The system that makes up the body produces some signs as it performs its various functions. These signs often do not convey easily understandable information out of the underlying complex biological structure and need to be processed and interpreted in order to examine various events in the body. Bioelectric signals relate to nerve conduction, brain, heart and various muscle movements, and etc. Ionic currents are the result of electrochemical events in some cells and are detected with the aid of electrodes, where after performing signal processing of the ionic currents, various diseases are diagnosed. To measure bioelectric potentials, we need transformers that convert electrical potential or current to ionic potentials and currents. Such a converter takes the form of two electrodes and measures the ionic potential difference between the points where the electrodes are applied.

In our patent application, which is subject to our invention, we use the Galvanic Skin Response (GSR) sensor to measure the muscle contraction signals mentioned above. At least two electrodes containing the GSR sensor are placed on the baby's body. These electrodes detect contractions for crying of the babies with colic during their sleep before they start crying. The start signal is automatically given by a microprocessor for white noise to be played to the babies. The contractions detected by the sensors are transmitted to the microprocessor as an information. Given the fact that each contraction is not likely to turn into a cry, information of a possibility of crying is transmitted to the microprocessor if there are more than 12 contractions per minute. The microprocessor starts to play white noise for the baby to listen to through headphones placed on the baby's ears. The white noise is recorded in memory or stored and accessed through a connected external media player. These headphones are placed in such a way that they will not create a weight on the baby's head and will not damage the skin.

The electrodes to be placed have the characteristics of measuring the difference between the width and the velocity of the measured waves, the depth and speed of the baby's breathing, and the measurement of the baby's heartbeat. Thus, the user defines the baby's age in number of months through the keys in the device interface. The data to be obtained from the baby's age in number of months is compared with the data obtained as a result of the measurements mentioned above and in case of any irregularity, the user is informed by sounds and by a digital visual display about the differences in measurements.

The invention claimed is:
1. A method for calming a crying of a baby using a computer system having a memory, a microprocessor, a digital visual display, and a user interface, wherein the computer system is communicably coupled to headphones to provide sounds to the headphones, the method comprising:

providing a recording of white noise from a media player or from the computer system;

providing a sensor in communication with the microprocessor, wherein the sensor is configured to measure muscle contractions of a baby, wherein the microprocessor is further configured to compare the muscle contractions of the baby with user input data entered into the user interface; and instructing, in response to a determination that a predetermined number of the muscle contractions of the baby is at least twelve contractions, the recording of the white noise to be played into the headphones on ears of the baby.

2. The method according to claim 1, wherein the media player is in communication with the computer system, and wherein when the recording of the white noise is provided from the media player, the recording of the white noise is played by the media player.

3. The method according to claim 1, wherein the headphones are earphones.

4. A system for calming a crying of a baby, the system comprising:

a microprocessor;

a computer having a memory for storing a recording of white noise; and a sensor in communication with the computer and configured to measure muscle contractions of the baby;

wherein the microprocessor is connected to the computer and is configured to:

instruct, in response to a determination that a predetermined number of the muscle contractions of the baby is at least twelve contractions, the recording of the white noise to be played into headphones on ears of the baby;

and compare the muscle contractions of the baby with user input data entered via a user interface.

5. The system according to claim 4, wherein the recording of the white noise is played by a media player that is in communication with the computer.

6. The system according to claim 4, wherein the headphones are earphones.

\* \* \* \* \*